United States Patent [19]

Fisher et al.

[11] Patent Number: 4,788,063
[45] Date of Patent: Nov. 29, 1988

[54] DRUG DELIVERY SYSTEM

[75] Inventors: Abraham Fisher, Holon; Drora Levy, Herzeliya B; Michael Y. Spiegelstein; Jacob Grunwald, both of Rehovot; Aharon Levy, Moshav Beith Hanan; Moshe Kushnir, Nir Zevi, all of Israel

[73] Assignee: State of Israel, Represented by Prime Minister's Office Israel Institute for Biological Research, Ness-Ziona, Israel

[21] Appl. No.: 760,609

[22] Filed: Jul. 30, 1985

[30] Foreign Application Priority Data

Aug. 14, 1984 [IL] Israel ........................................ 72684

[51] Int. Cl.[4] .............................................. A61F 13/02
[52] U.S. Cl. ....................................... 424/449; 424/448
[58] Field of Search ................ 424/448, 449; 514/946, 514/947

[56] References Cited

U.S. PATENT DOCUMENTS

| | | | |
|---|---|---|---|
| 4,338,306 | 7/1982 | Kitao et al. | 514/4 |
| 4,485,033 | 11/1984 | Kitao | 514/946 |
| 4,490,322 | 12/1984 | Zierenberg | 424/449 |
| 4,568,343 | 2/1986 | Leeper et al. | 424/449 |

Primary Examiner—Thurman K. Page
Assistant Examiner—L. R. Horne
Attorney, Agent, or Firm—Oblon, Fisher, Spivak, McClelland & Maier

[57] ABSTRACT

There is provided a composition for the transdermal application of basic drugs which have a high specific activity. The drug is provided in combination with a fatty acid having a low molecular weight. Amongst others, the delivery system is suited for cholinergic and anticholinergic basic drugs. The compositions can be supported by a pad, bandage or the like. It is one of the advantages of the compositions of the invention that a prolonged effect can be obtained, with an essentially constant therapeutic level of the active ingredient.

5 Claims, 2 Drawing Sheets

DURATION OF PERCUTANEOUS DELIVERY OF PHYSOSTIGMINE VERSUS INTRAMUSCULAR INJECTION IN PIGS.

○ = INTRAMUSCULAR INJECTION OF PHYSOSTIGMINE 125 ug/kg
▲ = PERCUTANEOUS DELIVERY OF PHYSOSTIGMINE IN 50 w/v % PROPIONIC ACID, 5 cm$^2$/kg.
● = PERCUTANEOUS APPLICATION OF PHYSOSTIGMINE IN PROPIONIC ACID 50 w/v-%, 3 cm$^2$/kg.

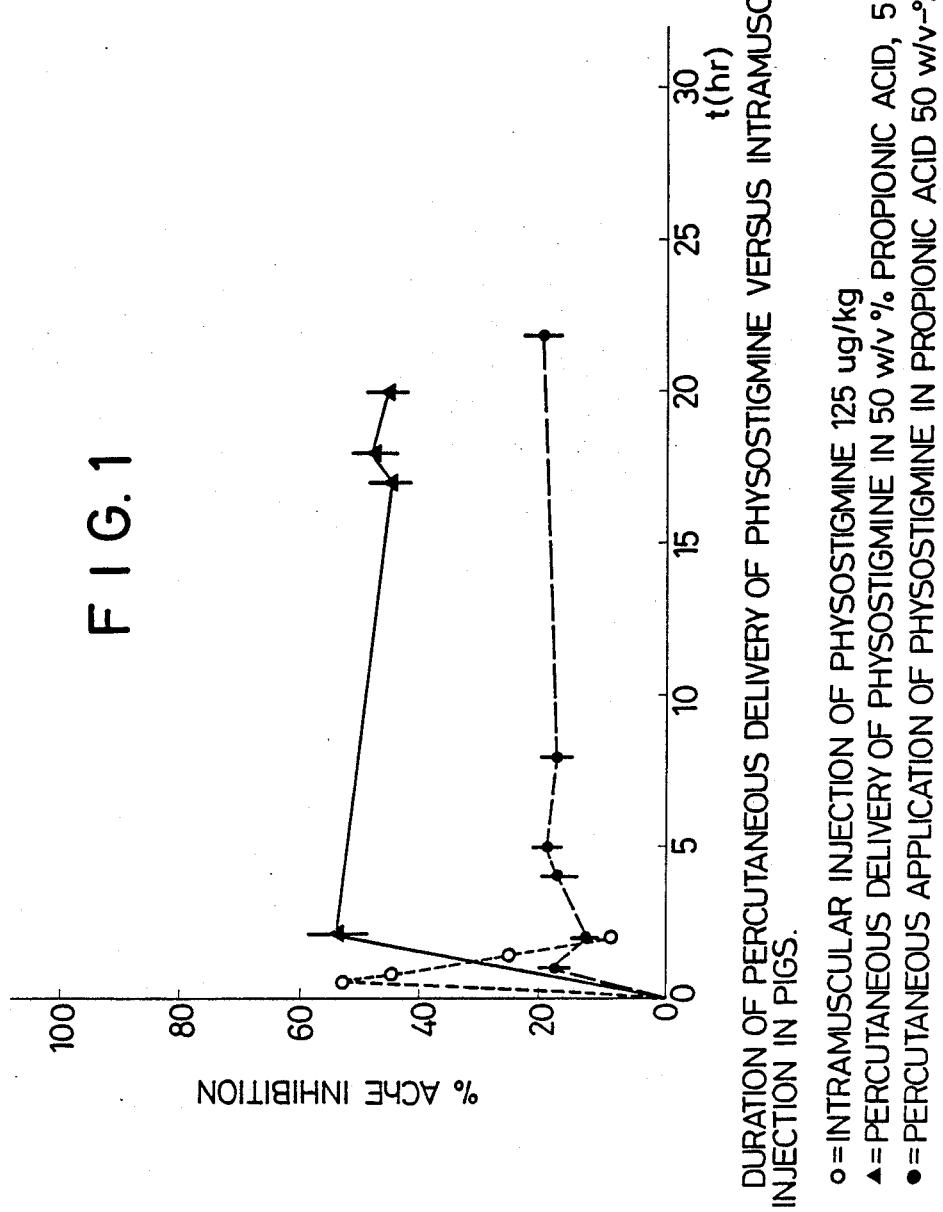

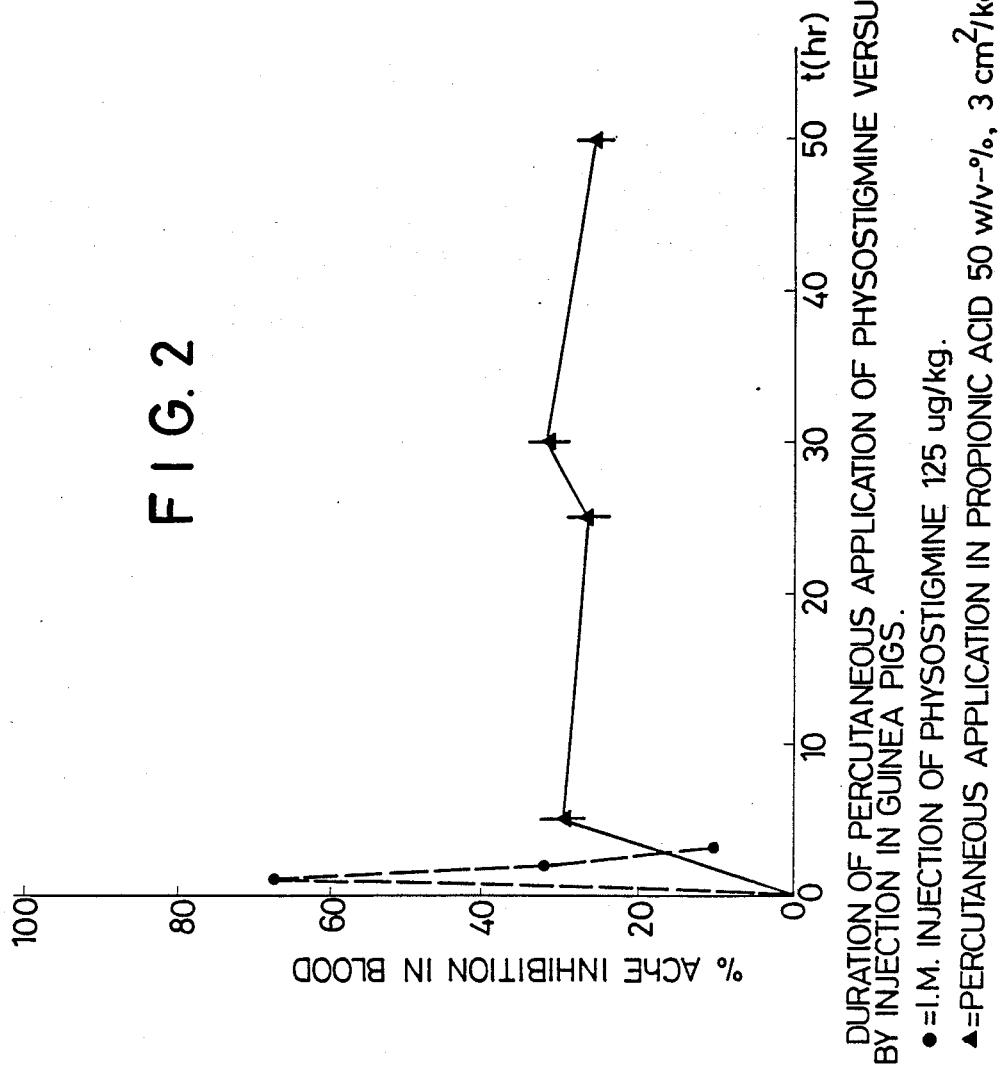

DRUG DELIVERY SYSTEM

FIELD OF THE INVENTION

There is provided a transdermal drug delivery system for drugs having a high potency, where a prolonged systemic activity is required. The transdermal delivery system is applicable to a variety of drugs, the preferred ones being cholinergic and anticholinergic agents. The drug delivery system is especially suited for the controlled transdermal delivery of active basic drugs, for the treatment of central and/or peripheral cholinergic disorders.

BACKGROUND OF THE INVENTION

A number of disease states have been identified as being associated with a cholinergic deficiency or alternatively hyperfunction (Table I). These include central as well as peripheral disorders. Recent studies have indicated that central cholindergic hypofunction may be involved in the pathology of senile dementia of Alzheimer's type (SDAT), and in other neurological and psychiatric disorders as listed in Table I, [A. Fisher and I. Hanin, Life Sci. 27, 1615 (1980); R. Bartus et al, Science 217, 408 (1982)].

TABLE I

THE INVOLVEMENT OF THE CHOLINERGIC NERVOUS SYSTEM IN VARIOUS DISEASE STATES

| Cholinergic Hypofunction | Hyperfunction |
|---|---|
| Senile Dementia of Alzheimer's Type (SDAT) (1) | Parkinson's Disease |
| | Pseudo Parkinson's Disease |
| Pick's Disease | Spasmodic Torticollis |
| Gerstmann-Straussler Syndrome | Depression |
| Down's Syndrome | Motion Sickness |
| Huntington's Chorea (1) | |
| Friedrich's Ataxia (1) | |
| Tardive Dyskinesia (1) | |
| Gilles de la Tourette Syndrome (1) | |
| Childhood Schizophrenia | |
| Anticholinergic Intoxication | Anticholinesterase Poisoning |
| Tricyclic Antidepressants Intoxication | |
| Myasthenia Gravis | |
| Eaton Lambret Syndrome | |
| Glaucoma | |
| Gastro-Intestinal Tract Disorders | Gastro-Intestinal Tract Disorder |
| Urinary Bladder Dysfunction | |
| Supranuclear Palsy | |

Whereas many drugs have been developed for treatment of peripheral cholinergic disorders, drug development for central cholinergic disorders, especially when a cholinergic hypoactivity is implicated, is still at its infancy. Since SDAT appears to be a primary cholinergic hypofunction, trials have been conducted in which ACh precursors (choline- or lecithin), acetylcholinesterase (AChE) inhibitors (physostigmine or tetrahydroaminoacridine), or direct acting agonists (arecoline) have been administered to SDAT patients because of the ability of these agents to elevate cholinergic activity in the brain. Although the results have not been conclusive as to the efficiency to the treatment with the above mentioned agents, some encouraging results were obtained with AChE inhibitors and direct acting agonists.

Unfortunately, some of these drugs, such as physostigmine, exhibit a short-half life, due to rapid metabolism following systemic administration. Moreover, physostigmine and some other cholinergic drugs, have a narrow therapeutic window (i.e. ratio between the medium toxic dose and the medium effective dose), and cause side effects which limit their systematic use. Some of the mentioned disorders require chronic treatment and thus the issue of side effects is critical.

Recently, physostigmine has been formulated for oral dosage in tablets. The almost inevitable result of oral administration of drugs is that the level of the drug in circulation surges to a high, each time the drug is administered, followed by a gradual decline in concentration in the blood and body.

A plot of drug concentration in blood following a dosage schedule of several tablets a day has the appearance of a series of peaks, which may surpass the toxic threshold, and minima which may be below the effective dose. To obtain the desired therapeutic effect, it is necessary to establish a dosage regime of multiple unit doses over a 24-hour period. This regime is of particular problem when dealing with demented patients, like SDAT patients.

Administration of cholinergic drugs by other routes, such as injection is inconvenient, painful, and due to their short life in the body, not practical, especially when there is a need for repeated injections.

One way to avoid the problems mentioned above is to administer systemically active drugs through the skin. The percutaneous route has attributes that are superior to other modes of systemic drug administration:

(1) It alllows a continuous administration of the drug to the circulation over a prolonged period of time;

(2) It provides an essentially stable drug level in the blood, thus limiting side effects due to overdosing, and lack of effect due to underdosing;

(3) It permits use of pharmacologically active agents with a short biological half life;

(4) It simplifies the medication regimen.

Despite these advantages, the transdermal mode of administration has not been widely used. Recently, however, a few transdermal delivery systems were developed. These include the transdermal delivery systems for scopolamine and for nitroglycerine (Chemical Week, September 26, 1984, P. 42).

The transdermal delivery of systemically active drugs through the skin has certain constraints which limit its wider application. The main one is the need for very potent drugs, since the skin represents a partial barrier to the passage of many substances. Thus, the most suitable drugs for controlled administration via this route, are those active at a parenteral dose of a few mgs per day or less.

Many cholinergic and anticholinergic drugs are effective at this dose range.

SUMMARY OF THE INVENTION

There is provided a transdermal pharmaceutical composition for the gradual controlled delivery of potent drugs. Drugs of choice for use with this system are cholinergic and anticholinergic basic drugs. The novel compositions are adapted to maintain a prolonged therapeutic effect at a predetermined systemic level within a certain desired range. The delivery systems according to the invention decrease side effects compared with parenteral applications. The compositions according to the invention comprise in combination a low molecular weight fatty acid and the effective ingredient. The fatty acid or combination of acids serves as solvent for the basic drug and as effective transport vehicle for the transdermal administration of the drug, which otherwise would not penetrate the skin barrier.

It is possible to maintain an essentially constant therapeutic level of the drugs with such delivery systems, over a predetermined period of time. Patient intervention is required only for initiation and termination. The percutaneous delivery system (PDS) according to the invention is applicable to a wide variety of pharmaceutically active substances, both for use in human and veterinary medicine.

Amongst cholinergic agents which can be administered there may be mentioned: physostigmine, tetrahydroaminoacridine, arecoline, oxotremorine, pilocarpine, acceclidine or combination of any of these.

Amongst anticholinergic agents there may be mentioned: scopolamine, atropine, benztropine, aprophen, artane, trihexyphenidyl and benactyzine.

The active ingredient or ingredients are used in a vehicle, such as lower fatty acids, which serve both as solvent and as transdermal delivery agent. Amongst fatty acids there may be mentioned: all lower alkanoic acids having from 2 to 10 carbon atoms, and especially acids like propionic acid, valproic acid, or a combination of any of these.

The invention is also applicable to the delivery of antimuscarinic drugs, such as scopolamine benztropine, artane, aprophen, trihexyphenidyl, benactyzine, which can be used in brain disorders listed in Table 1, in which a cholinergic hyperactivity has been implicated, and for treatment of conditions wherein central dopaminergic activity is pathologically reduced.

Physostigmine, by itself or in combination with other drugs, can also be used to manipulate the activity of acetylcholinesterase under conditions in which a transient partial activity is desired.

BRIEF DESCRIPTION OF THE DRAWINGS

In the drawings:
FIG. 1 shows duration of percutaneous delivery of physostigmine versus intramuscular injection in pigs; and
FIG. 2 shows duration of percutaneous application of physcostigmine versus application by injection in guinea pigs.

DESCRIPTION OF THE PREFERRED EMBODIMENT

The following examples are intended to illustrate the present invention and these are to be construed in a non-limitative manner.

EXAMPLE 1 Physostigmine Delivery System

To 1 g of pure physostigmine base, 1 ml of pure propionic acid was added. The mixture was stirred till a complete clear solution was obtained. The resulting solution does not cause irritation as determined by the guinea pigs test.

EXAMPLE 2 Polypharmaceutical Approach: e.g. Physostigmine: Arecoline: Propionic Acid To 1 g physostigmine base, 1 ml of pure propionic acid and 1 g arecoline base were added. A base was prepared from arecoline hybromide. The resulting solution was used for percutaneous drug delivery.

In a similar manner, other colinergic and anticholinergic compounds were dissolved in propionic acid, butyric acid, valproic acid or in other low molecular weight organic acids.

A typical experiment was performed as follows:
Laboratory animal species used throughout this study consisted of albino guinea pigs of either sex of a local strain, (Dunkin-Hadley origin), weighing between 300–400 g, and female pigs of the large White and Lundrace strain, 8–12 weeks of age, weighing 8–14 kg.

At 30 minutes prior to dermal application of test solutions, the hair at the test sites was closely clipped. Only animals in which the skin at the test sites appeared grossly normal and was free of bites, scratches or bruises, were selected for the study.

Treatment solutions for dermal application were freshly prepared and applied to a pre-determined area of a commercially available pad, (micropad dressing 3M No. 1610, U.S. Pat. No. 3,285,245) which in turn was secured to dorsal test-sites by an adhesive bandage, serving at the same time as an occlusive dressing. Blood samples for acetylcholinesterase measurements were obtained at specified times, by cardiac puncture in guinea-pigs, and by venipuncture from the superior venacava in pigs. Intervals between bleedings were 2 hours in guinea pigs, and 30 minutes in pigs. The total volume of blood withdrawn at each bleeding did not exceed 0.5 ml in guinea pigs and 3 ml in pigs.

Cholinesterase Determinations: Whole blood cholinesterase activity was determined by the method of Ellman [G.L. Ellman et al, Biochem. Pharmacol. 7, 83 (1961)], or by that described by Johnson and Russell [C.D. Johnson and R. L. Russell, Anal Biochem 64, 229 (1975)]. Data obtained in experimental animals (guinea pigs and pigs) show a remarkable prolonging of the duration of action of the dermally applied drug when compared with systemic administration. Thus, when physostigmine in propionic acid (50% w:v) was applied to the skin of guinea pigs and pigs, it maintained a steady concentration of the drug in the blood for several days.

Duration of the effect following intramuscular injection was 2-3 hours (FIG. 1, 2).

The rate of penetration of physostigmine in propionic acid (50% w:v) into the blood when applied dermally to pigs (5–6 $cm^2$/kg) was 30–40 $\mu$g/kg hr.

Under these experimental conditions, about 50% inhibition in blood cholinesterase was achieved.

Infusion of physostigmine in SDAT patients, that caused improvement in memory disorders, was achieved following intravenous infusion at a rate of 3.4–14 $\mu$g/kg. hr.

Acetylcholinesterase activity in SDAT patients is reduced in selected brain areas, such as the cortex and hippocampus, in particular. Therefore, the CPD should effect mainly these brain areas and render other regions relatively unaffected, due to the fact that only minute amounts of the drug are delivered at each time point during treatment.

In practicing this invention, one can employ any systemically active basic cholinergic or anticholinergic drug which will be absorbed through the skin once it is dissolved in propionic acid or another low molecular weight fatty acid (with or without additives).

The amount of an active drug penetrating the skin at a given time depends on the area of application, on the concentration of the active drug in the vehicle, and on the nature of the vehicle and the bandage system.

Description of the Bandage System to be used for CPD:

A specific bandage system was designed by the inventor, consisting of a reservoir of the active drug(s) in the vehicle, a protective impermeable barrier film and a diffusion control membrane. The protective film is made of Parylene (Union Carbide, U.S. Pat. Nos. 3,288,728 and 3,342,754). The outer layer is made of a flelible polymer such as polypropylene or polyethylene, which is impermeable to the drug used and prevents its leakage. The inner layer of the reservoir is a diffusion control membrane, which controls the rate of delivery of the drug to the skin. This membrane is again covered with a protective film to be removed before use.

We claim:

1. A pharmaceutical composition for transdermal application of, as the active ingredient, a drug of high intrinsic specific activity comprising in combination said active ingredient and a low molecular weight $C_2$-$C_{10}$ fatty acid, said active ingredient being a cholinergic or anticholinergic agent selected from the group consisting of physostigmine, tetrahydroaminoacridine, arecoline, oxotremorine, pilocarpine, acceclidine, scopolamine, atropine, benztropine, aprophen, artane, trihexyphenidyl and benactyzine.

2. A bandage or pad composition according to claim 1, wherein the fatty acid is selected from $C_2$ to $C_{10}$—lower alkanoic acids.

3. A bandage or pad composition according to claim 1 wherein the active ingredient comprises from about 10 weight-% to about 70 weight—% of the composition.

4. A bandage or pad composition according to claim 1, wherein the bandage or pad comprises a reservoir inner layer and a protection impermeable barrier protective film.

5. A bandage or pad composition according to claim 4, wherein between the reservoir and the skin there is provided a diffusion control membrane and a removable impermeable membrane.

* * * * *